(12) United States Patent
Kaski

(10) Patent No.: US 10,729,350 B2
(45) Date of Patent: Aug. 4, 2020

(54) SYSTEM AND METHOD FOR MONITORING CARDIAC ARRHYTHMIAS

(71) Applicant: General Electric Company, Schenectady, NY (US)

(72) Inventor: Mikko Kaski, Helsinki (FI)

(73) Assignee: General Electric Company, Schenectady, NY (US)

( * ) Notice: Subject to any disclaimer, the term of this patent is extended or adjusted under 35 U.S.C. 154(b) by 141 days.

(21) Appl. No.: 15/925,458

(22) Filed: Mar. 19, 2018

(65) Prior Publication Data

US 2019/0282118 A1    Sep. 19, 2019

(51) Int. Cl.
| | |
|---|---|
| A61B 5/00 | (2006.01) |
| A61B 5/0452 | (2006.01) |
| A61B 5/0295 | (2006.01) |
| A61B 5/0245 | (2006.01) |
| A61B 5/1455 | (2006.01) |
| A61B 5/021 | (2006.01) |

(52) U.S. Cl.
CPC .......... *A61B 5/0452* (2013.01); *A61B 5/0295* (2013.01); *A61B 5/746* (2013.01); *A61B 5/021* (2013.01); *A61B 5/0245* (2013.01); *A61B 5/14552* (2013.01)

(58) Field of Classification Search
None
See application file for complete search history.

(56) References Cited

U.S. PATENT DOCUMENTS

| | | | |
|---|---|---|---|
| 6,490,479 | B2 | 12/2002 | Bock |
| 7,702,382 | B2 | 4/2010 | Xue et al. |
| 7,806,832 | B2 | 10/2010 | Gallagher et al. |
| 7,846,106 | B2 | 12/2010 | Andrews et al. |
| 8,352,018 | B2 | 1/2013 | Xue et al. |

(Continued)

OTHER PUBLICATIONS

GE Healthcare, "GE EK-Pro Arrhythmia Algorithm", DOC0783131, 2010 General Electric Company.

(Continued)

*Primary Examiner* — George Manuel
(74) *Attorney, Agent, or Firm* — Andrus Intellectual Property Law, LLP

(57) ABSTRACT

A patient monitoring system for monitoring cardiac arrhythmias includes an ECG monitor configured to monitor cardiac potentials during cardiac cycles and an arterial blood flow monitor configured to monitor arterial blood flow and generate pulse waveform. The system further includes an arrhythmia detection module that detects the presence of an arrhythmia based on the cardiac potentials and generates an arrhythmia indicator, and an arrhythmia analysis module that assesses the severity of the detected arrhythmia. The arrhythmia analysis module calculates average sinus pulse information based on the pulse waveform data for two or more cardiac cycles occurring when no arrhythmia is detected, and then calculates average arrhythmia pulse information based on pulse waveform data for two or more cardiac cycles occurring after detection of the arrhythmia. The average arrhythmia pulse information is then compared to the average sinus pulse information and an arrhythmia severity indicator is generated based on the comparison.

20 Claims, 8 Drawing Sheets

(56) References Cited

U.S. PATENT DOCUMENTS

2014/0135859 A1* 5/2014 Bardy .................. A61B 5/0006
607/3
2017/0367602 A1* 12/2017 Sullivan .................. G06F 19/00

OTHER PUBLICATIONS

Xue, Joel, "System and Method for Detecting Atrial Fibrillation", unpublished U.S. Appl. No. 15/631,895, filed Jun. 23, 2017.

* cited by examiner

SYSTEM AND METHOD FOR MONITORING CARDIAC ARRHYTHMIAS

BACKGROUND

This disclosure generally relates to the field of patient monitoring and, more particularly, to systems and method for monitoring and assessing cardiac arrhythmias.

Currently available patient monitoring systems including electrocardiographs (ECG) typically have algorithms for detecting and identifying various arrhythmias. One very common and sometimes critical arrhythmia is atrial fibrillation (AFIB). AFIB is the most common cardiac arrhythmia resulting in hospitalization in the United States. AFIB is often identified by irregular heart rhythm and is clinically defined as uncoordinated contractions of the atria. With critically ill patients AFIB may be serious due to week circulation of the blood during the arrhythmia. In these cases, immediate action by caregivers may be needed. Patients often experience palpitations and have an increased risk of stroke. AFIB puts patients at significant risk because it allows blood to pool and stagnate in the left atrium and, thus, form a clot. This clot can slough off and travel up to the brain where it can block sufficient blood flow to a portion of the brain where upon it will begin to die, thus causing a stroke. AFIB is estimated to cause up to a quarter of all strokes and is often undetected until a stroke occurs. It is estimated that approximately a third of patients experiencing AFIB are asymptomatic.

AFIB requires aggressive treatment. The longer a patient is in AFIB, the more likely they are to remain in AFIB, making early detection desirable. Prompt detection of the onset of AFIB provides an opportunity for therapy during the first 48 hours when expensive antithrombolic treatments may not be necessary because the formation of blood clots has not yet occurred in the atria. The prevalence of AFIB is high and age dependent, from 0.7% in the ages 55-59 to 17.8% for 85 years or older. Yet, AFIB is notoriously hard to detect. The most common method for automatically detecting AFIB in ECG recordings relies heavily on the fact that AFIB is a chaotic atrial arrhythmia, randomly conducted to the ventricles. As such, the time periods between features of the QRS waves, as measured by the RR intervals, should be continuously varying in the presence of AFIB. It is this attribute of AFIB, that it is a continuously chaotic rhythm, that is used by most ambulatory ECG analysis programs to detect AFIB. However, RR intervals of normally conducted beats can vary for other types of benign arrhythmias that are not AFIB. Examples include premature atrial complexes (PACs) or sinus arrhythmia (SA), which are both quite common in the normal population. While these benign arrhythmias do exhibit as variability in RR intervals, these arrhythmias are typically benign and do not pose a serious health concern.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

One embodiment of a patient monitoring system for monitoring cardiac arrhythmias includes an ECG monitor configured to monitor cardiac potentials during cardiac cycles and an arterial blood flow monitor configured to monitor arterial blood flow and generate pulse waveform. The system further includes an arrhythmia detection module that detects the presence of an arrhythmia based on the cardiac potentials and generates an arrhythmia indicator, and an arrhythmia analysis module that assesses the severity of the detected arrhythmia. Specifically, the arrhythmia analysis module calculates average sinus pulse information based on the pulse waveform data for two or more cardiac cycles occurring when no arrhythmia is detected, and then calculates average arrhythmia pulse information based on pulse waveform data for two or more cardiac cycles occurring after detection of the arrhythmia. The average arrhythmia pulse information is then compared to the average sinus pulse information and an arrhythmia severity indicator is generated based on the comparison.

One embodiment of a method of monitoring cardiac arrhythmia includes measuring cardiac potentials with an ECG monitor during cardiac cycles and measuring arterial blood flow for the cardiac cycles with an arterial blood flow monitor to generate pulse waveform data. Average sinus pulse information is then calculated based on pulse waveform data for two or more cardiac cycles for which no arrhythmia is detected. Once the presence of an arrhythmia is detected, average arrhythmia pulse information is calculated based on pulse waveform data for two or more cardiac cycles following the detection. The average arrhythmia pulse information is then compared to the average sinus pulse information to generate an arrhythmia severity indicator.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

The inventor has recognized that given the prevalence of arrhythmias, including AFIB, measurement of the severity of the AFIB can be important to maximize the effectiveness of patient monitoring and to facilitate detection and treatment of the most severe arrhythmias. The severity of an arrhythmia depends on its effect on the blood circulation in the patient's body. For example, the most critical AFIB incidence may cause circulation to temporarily stop, while less critical arrhythmias may maintain consistent circulation at the appropriate level for the patient. Thus, the inventor recognized that the severity of an arrhythmia, and thus its criticality to the patient's current health condition, can be measured according to its effect on hemodynamics.

Moreover, the inventor realized that such information can provide valuable information for real-time patient monitoring, and that such information can be immediately reported at part of the patient physiological monitoring and incorporated into alarming algorithms so that clinicians can be informed of the severity of an arrhythmia event and alerted to the most severe events. As disclosed herein, a pulse waveform data from an arterial blood flow monitor is correlated to cardiac potentials from an ECG monitor. Average pulse information is established for the patient based on pulse waveform data gathered during a period of sinus cardiac rhythm for the patient, thus establishing a baseline blood flow value for the patient during normal sinus rhythms (NSR). Once AFIB is detected, pulse waveform data is gathered and average arrhythmia pulse information is determined for two or more cardiac cycles occurring after the arrhythmia has been detected. The arrhythmia severity is then determined by comparing the average sinus pulse information to the average arrhythmia pulse information.

Figure 1:
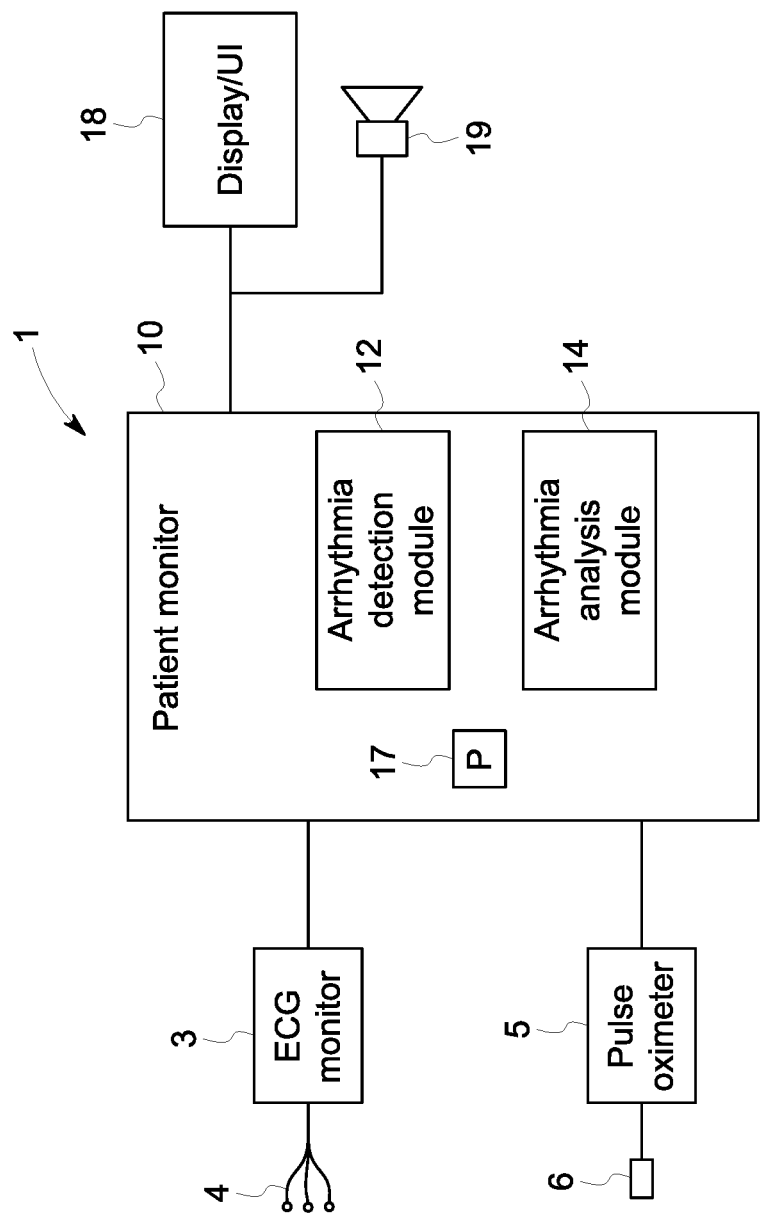
FIG. 1 schematically depicts an exemplary patient monitoring system for monitoring cardiac arrhythmias.

FIG. 1 schematically depicts an exemplary patient monitoring system 1 for monitoring cardiac arrhythmias. In the exemplary embodiment, the patient monitoring system 1 includes a patient monitor 10 receiving information from an ECG monitor 3 and an arterial blood flow monitor 5, which in the depicted embodiment is a pulse oximeter. The cardiac potentials generated by the ECG monitor 3 and the pulse waveform generated by the arterial blood flow monitor 5 are provided to a patient monitor 10 that gathers, correlates, and analyzes the cardiac and pulse information. In various embodiments, the ECG monitor 3 and/or the arterial blood flow monitor 5 may be incorporated in a single, multi-parameter patient monitor 10 that receives the cardiac and pulse waveform information collected from the patient and generates the cardiac potentials and pulse waveform data accordingly. In other embodiments, the patient monitor 10 may be a separate device (such as a hub or central patient monitor device) that receives information from various separate monitors receiving and analyzing patient physiological data, including the ECG monitor 3 and the arterial blood flow monitor 5. In still other embodiments, the ECG monitor 3 and the arterial blood flow monitor 5 may communicate with one another to provide comprehensive patient monitoring, and each device may then communicate the patient monitoring information to the patient's medical record, such as stored on the network of the healthcare facility and/or on the cloud. For example, the ECG monitor 3 may incorporate the arrhythmia detection module 12 to detect an arrhythmia, and may communicate information regarding arrhythmia detection and the timing of the QRS wave to the arterial blood flow monitor 5. The arterial blood flow monitor 5 may similarly incorporate the arrhythmia analysis module 14 to determine an arrhythmia severity indicator as described herein.

The ECG monitor is recording and measuring cardiac potentials from a patient via two or more electrodes 4 connected to the patient. Various forms of ECG electrodes 4 and/or electrode systems are well known and available in the art, any of which may be utilized to record cardiac potentials from the patient. Additionally, any number of two or more ECG electrodes 4 may be utilized. In one embodiment, 10 ECG electrodes 4 are connected to the patient, and the ECG monitor 3 is configured to generate a standard 12 lead ECG. In other embodiments, fewer electrodes may be utilized and cardiac potentials may be generated for a smaller number of leads by the ECG monitor 3.

The arterial blood flow monitor 5 measures arterial blood flow for the patient and generates pulse waveform data representing blood flow changes during the cardiac cycles. In the depicted embodiment, the arterial blood flow monitor 5 is a pulse oximeter. In other embodiments, the arterial blood flow monitor 5 may be an invasive blood pressure monitor. The pulse oximeter 5 is connected to a pulse oximetry probe 6 that attaches to a patient, such as the patient's finger or ear, to measure the blood flow at that location during the cardiac cycles. Such probe 6 are well known in the art, often utilizing red and infrared light to measure changes in blood flow throughout the cardiac cycle.

The pulse oximeter and/or invasive blood pressure monitor then generate pulse waveform data representative of arterial blood flow during the cardiac cycles monitored by the ECG monitor. The cardiac potentials and the pulse waveform data can be synchronized according to the time of recordal, and thus correlations can be drawn between the cardiac cycles as measured by the cardiac potentials and the resulting measured blood flow at the measurement location of the arterial blood flow monitor 5.

In the depicted embodiment, the patient monitor 10 includes an arrhythmia detection module 12 and an arrhythmia analysis module 14, both being sets of software instructions configured to perform certain functions. The arrhythmia detection module 12 processes the cardiac potentials from the ECG monitor 3 to detect that presence or absence of an arrhythmia, and to generate an arrhythmia indicator upon detecting the presence of the arrhythmia. Thus, the arrhythmia detection module 12 informs the arrhythmia analysis module 14 when an arrhythmia is occurring, and such information is used to trigger analysis of the severity of the arrhythmia by the arrhythmia analysis module 14.

Various such arrhythmia detection modules 12 are available and known in the art for analyzing ECG potentials and detecting arrhythmias based thereon. For example, the Marquette 12SL® ECG analysis program by General Electric Company of Schenectady, N.Y., is an exemplary computerized analysis program providing measurements of heartrate, axis, intervals, and durations of heartrate waveforms, as well as interpretive statements offering automated ECG data analysis, such as arrhythmia detection, pace detection, waveform feature identification, etc. Other systems and software products are well known and available in the art providing arrhythmia detection.

Figure 5:
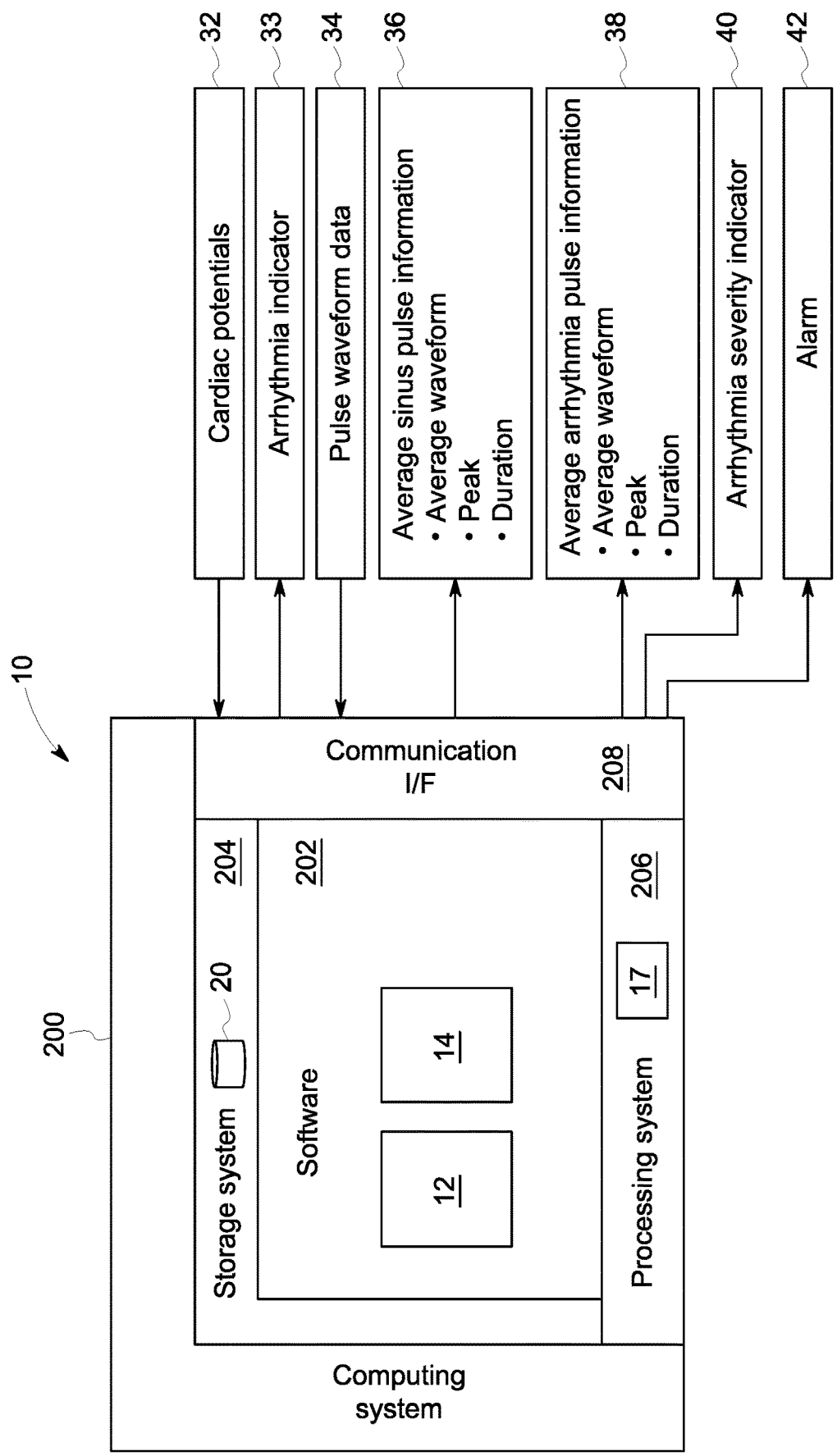
FIG. 5 is a block diagram illustrating an exemplary computing system of a patient monitoring system monitoring cardiac arrhythmias of a patient.

With further reference to FIG. 5, the arrhythmia analysis module 14 is a set of software instructions configured to calculate average sinus pulse information 36 based on pulse waveform data 34 for two or more cardiac cycles occurring during sinus rhythm, when no arrhythmia is detected. The arrhythmia analysis module 14 is then configured to, upon receiving an arrhythmia indictor 33 generated by the arrhythmia detection module 12, calculate average arrhythmia pulse information 38 based on pulse waveform data 34 for two or more cardiac cycles occurring after the arrhythmia indicator 33. The arrhythmia analysis module 14 is executable to compare the average sinus pulse information 36 calculated prior to detecting the arrhythmia with the average arrhythmia pulse information 38 calculated during an ongoing arrhythmia event to generate an arrhythmia severity indicator 40 indicating the clinical severity of the detected arrhythmia event.

In various embodiments, the arrhythmia severity indicator 40 may be generated upon receiving pulse waveform data 34 for at least a predetermined number of cardiac cycles following the arrhythmia detection, such as a number of cardiac cycles determined to provide enough pulse waveform data 34 to reliably determine the arrhythmia severity indicator 40. In such an embodiment, the arrhythmia severity indicator 40 may be continually updated during the arrhythmia event to account for pulse waveform data 34 generated for cardiac cycles where the arrhythmia indicator 33 continues to be present. Thus, the arrhythmia severity indicator 40 can provide an ongoing assessment of the arrhythmia severity throughout occurrence of an arrhythmia event or a patient. This may provide additional information about the progression of an arrhythmia event. Similarly, the arrhythmia severity indicator 40 may be calculated at predetermined points during an arrhythmia event, such as at certain intervals of cardiac cycles where the arrhythmia indicator is continuously detected and/or at predetermined time intervals during continuous detection of an arrhythmia. Alternatively or additionally, the arrhythmia analysis module 14 may be configured to wait until termination of the arrhythmia event (e.g., when the arrhythmia indicator is not longer present) to generate the arrhythmia severity indictor 40, where the average arrhythmia pulse information 38 is generated based on all pulse waveform data 34 for the cardiac cycles during the arrhythmia event.

Once generated, the arrhythmia severity indictor 40 is provided on a user interface display 18 to inform the clinician of the severity of the arrhythmia. In various embodiments, the arrhythmia indicator 40 may include a comparison graph depicting an average sinus pulse waveform and an average arrhythmia pulse waveform on a shared time axis, thereby providing a visual comparison between the two waveforms on a single time axis. FIG. 4B provides an exemplary comparison graph 41 comparing an exemplary average sinus pulse waveform 44 and an exemplary average arrhythmia pulse waveform 48. Alternatively or additionally, the arrhythmia severity indicator 40 may include one or more values determined based on various measurement differences between the average sinus pulse waveform 44 and the average arrhythmia pulse waveform 48. For example, the severity indicator value(s) may be based on one more of a peak amplitude difference 53, a peak time difference 54, and/or a difference integral of the area 56 between the average sinus pulse waveform 44 and the average arrhythmia pulse waveform 48.

With reference also to FIG. 5, the patient monitor 10 comprises a computing system 200 executing software 202 that performs the functions described herein, including the arrhythmia detection module 12 and the arrhythmia analysis module 14. The software receives the cardiac potentials 32, such as from the ECG monitor 3, which are processed by the arrhythmia detection module 12 to generate the arrhythmia indicator 33. The pulse waveform data 34 is also received from the arterial blood flow monitor 5. As described herein, the arrhythmia analysis module 14 analyzes the pulse waveform data 34 based on the cardiac pulse timing determined based on the cardiac potentials 32 and the presence/absence of an arrhythmia indicator 33 to determine average sinus pulse information 36 and the average arrhythmia pulse information 38. Each set of average pulse information 36, 38 may comprise any one or more of an average waveform, peak amplitude and time information, waveform duration, and/or other information regarding the morphology and/or timing of the average blood pulse occurring during the respective analysis period. The arrhythmia analysis module 14 is further configured to generate an arrhythmia severity indictor 40 based on a comparison between the average sinus pulse information 36 and the average arrhythmia pulse information 38. In certain embodiments, the arrhythmia analysis module 14 may be further configured to compare the arrhythmia severity indictor to one or more severity thresholds, and to generate one or more arrhythmia severity alarms 42 when the arrhythmia severity indicator 40 exceeds a respective severity threshold.

Figure 2:
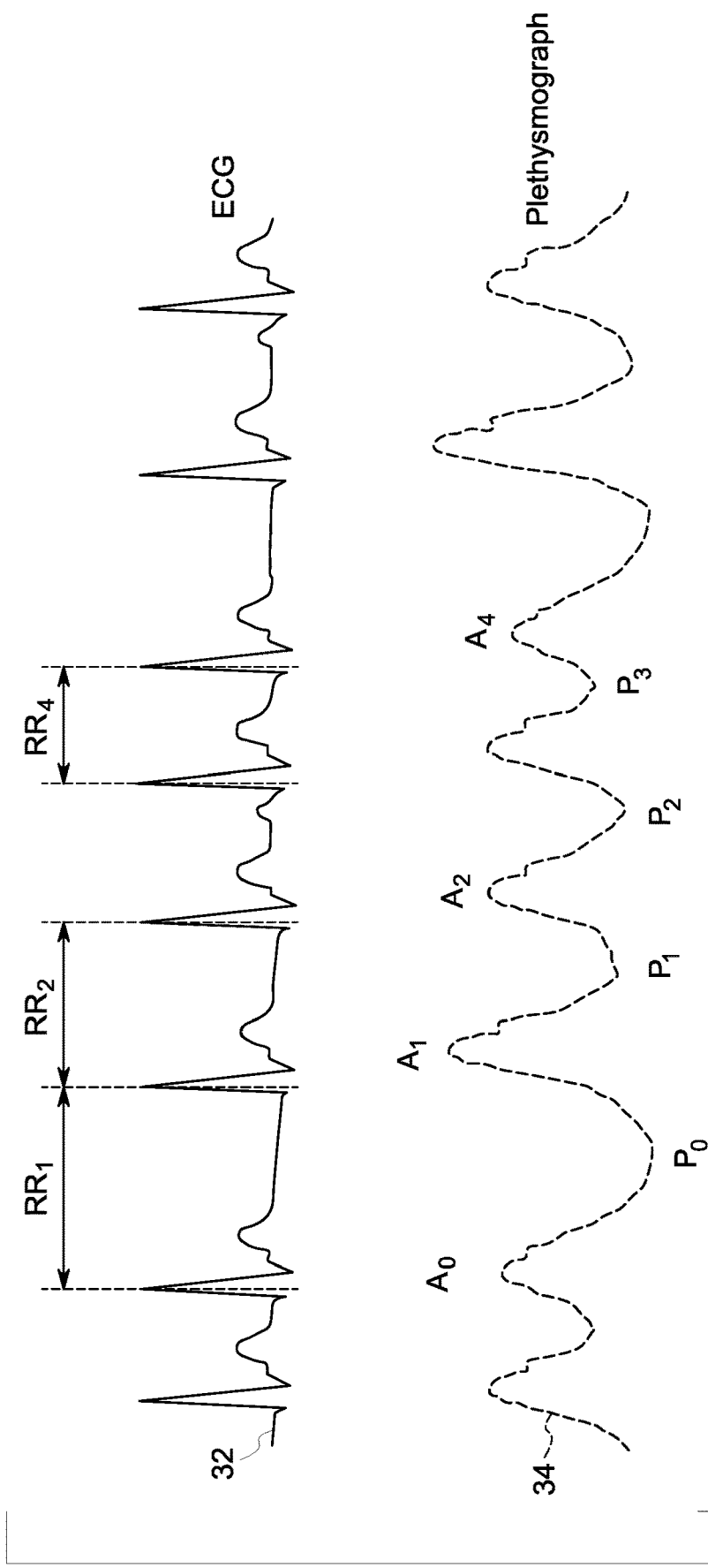
FIG. 2 is a graphical comparison of cardiac potentials from an ECG monitor and pulse waveform data from a plethysmograph.

FIG. 2 illustrates the impact of an arrhythmia on a distal plethysmograph pulse. The fir RR interval, $RR_1$, seen in the cardiac potentials 32, is longer than the preceding interval that generated pulse $A_0$. As a result, there is more time for the arterial blood to flow passively into the venous system. This produces a lowered blood volume at a diastole ($P_0$). The long RR interval also allows for a longer filing time in the left ventricle of the heart. By Starling's Law, the increased volume in the ventricle results in a more forceful ejection of larger amplitude of the next volume pulse $A_1$.

The following RR interval ($RR_2$) is shorter than the preceding interval. Since there is less time for blood to flow out of the arterial system, the pulse level at $P_1$ does not drop to as low of a value at diastole as the preceding pulse. The short filing time results in a lower stroke volume and a systolic pressure (compared to the preceding interval), which is reflected in the lower amplitude at $A_2$. Interval $RR_4$ illustrates an even shorter interval, with a resulting higher level at $P_3$ and reduced amplitude at $A_4$.

Changes in the pulse waveform are indicative of the effect that each arrhythmic cardiac cycle is having on perfusion. Accordingly, the inventor recognized that the pulse waveform data 34 could be examined to assess the severity of an arrhythmia. For example, the inventor developed a system that averages the pulse waveform data 34 over several arrhythmic cardiac cycles to provide representative information about how the arrhythmia is affecting the patient's perfusion, and thus the overall criticality to the patient's health resulting from the arrhythmia. Namely, sustained higher blood volume at the diastole P and reduced pulse amplitude A over a period of time means that the patient's profusion is insufficient. This information will be reflected in the average arrhythmia pulse information 38 and the arrhythmia severity indictor 40.

Figure 3:
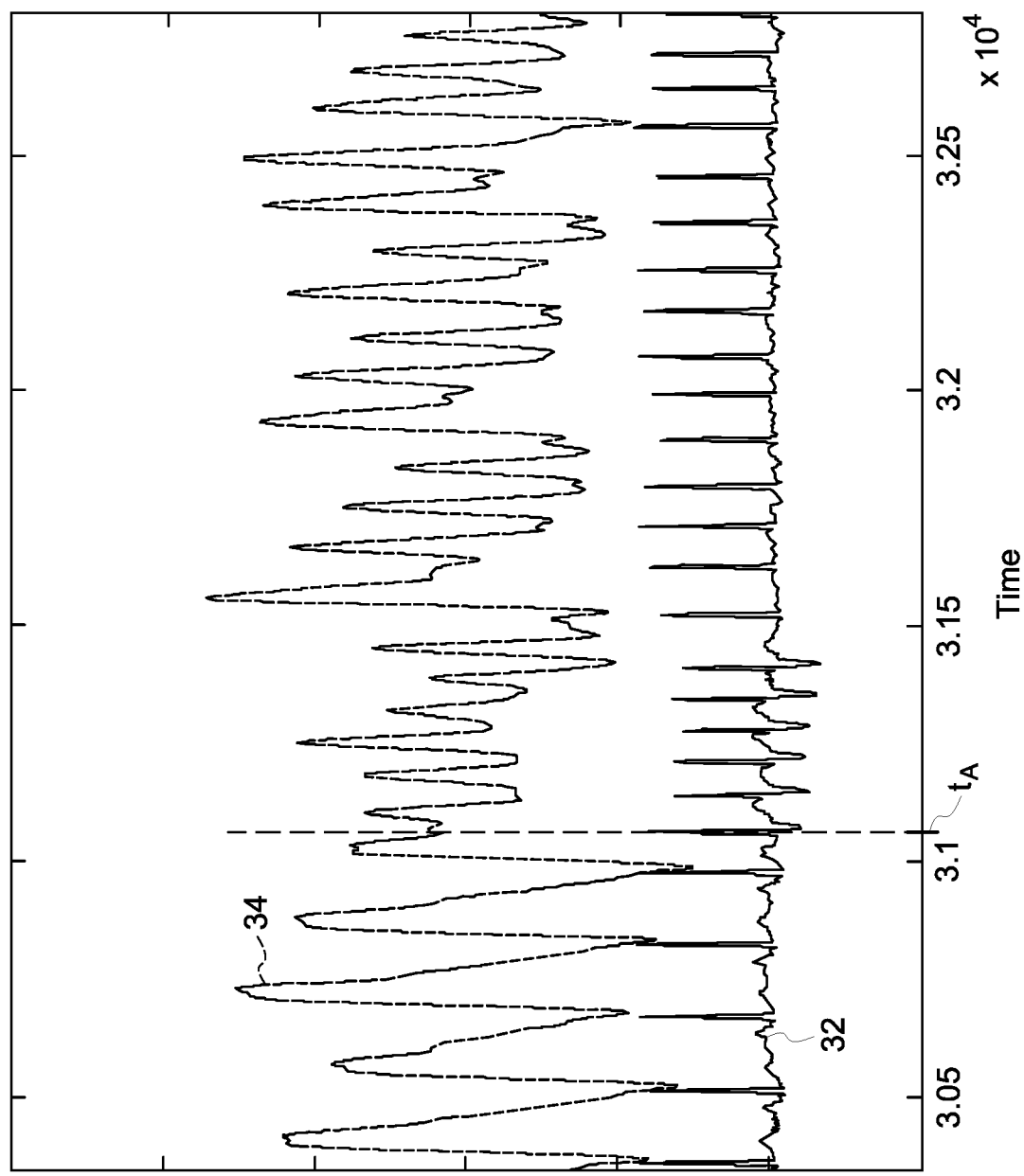
FIG. 3 is an additional graphical comparison showing cardiac potentials and pulse waveform data before and after an arrhythmia detection.

FIG. 3 depicts corresponding cardiac potentials 32 and pulse waveform data 34 over a single period of time. The cardiac potentials 32 represent a sinus rhythm at the beginning of the time period until an arrhythmia is detected at time $t_A$. In certain embodiments, the arrhythmia detection module 12 may require two or more arrhythmic cardiac cycles to proceed before the arrhythmia is detected (e.g. to be able to determine that the rhythm is chaotic and indicative of AFIB). In various embodiments, the arrhythmia indicator 33, and the time in the cardiac data where the arrhythmia is flagged, may be at the time of detection and/or associated with the most recent cardiac cycle comprising the arrhythmia detection analysis. Alternatively, the arrhythmia indicator 33 may be marked at a time prior to detection, such as the first cardiac cycle at which post-detection analysis determines that the arrhythmia was initiated.

The arrhythmia analysis module 14 determines the average sinus pulse information 36 prior to the time $t_A$ of arrhythmia detection and begins determination of the average arrhythmia pulse information 38 after the time $t_A$ of the arrhythmia detection. As can be seen in the pulse waveform data 34, the arterial blood flow for the cardiac cycles following the time $t_A$ of arrhythmia detection are different than the relatively steady and consistent waveforms prior to the time $t_A$ of the arrhythmia.

The average pulse information is determined by dividing the pulse waveform data 34 into sections based on the cardiac cycles. For example, division of the pulse waveform data 36 into time sections (predetermined durations of pulse waveform data 36) may be based on QRS detection of the cardiac potentials 32. QRS detection may be performed by the arrhythmia detection module 12, for example, or by the arrhythmia analysis module 14, or by a separate set of software instructions (such as a program set dedicated to QRs detection, waveform parsing, and/or rhythm detection). For example, the time sections of pulse waveform data 34 may be a predetermined duration following detection of a particular waveform feature, such as the P, Q, or R waves. Similarly, the time section of pulse waveform data may be generated based on detection of the R wave peak, such as a predetermined amount of time prior to the identified R peak and a predetermined amount of time following the identified R peak, such as an amount of time surrounding the R peak detection representing the time QT interval.

Mathematical calculations may then be performed based on the time sections of pulse waveform data to determine the average pulse information 36, 38. For example, the pulse waveform data 36 for a predetermined time during a QRS waveform may be isolated for each cardiac cycle, and the isolated data sections may be averaged to create an average pulse waveform 44, 48, which may be an average sinus pulse waveform 44 if based on data occurring during normal sinus rhythm (NSR) or an average arrhythmia pulse waveform 48 if occurring during arrhythmia detection.

Figure 4A:
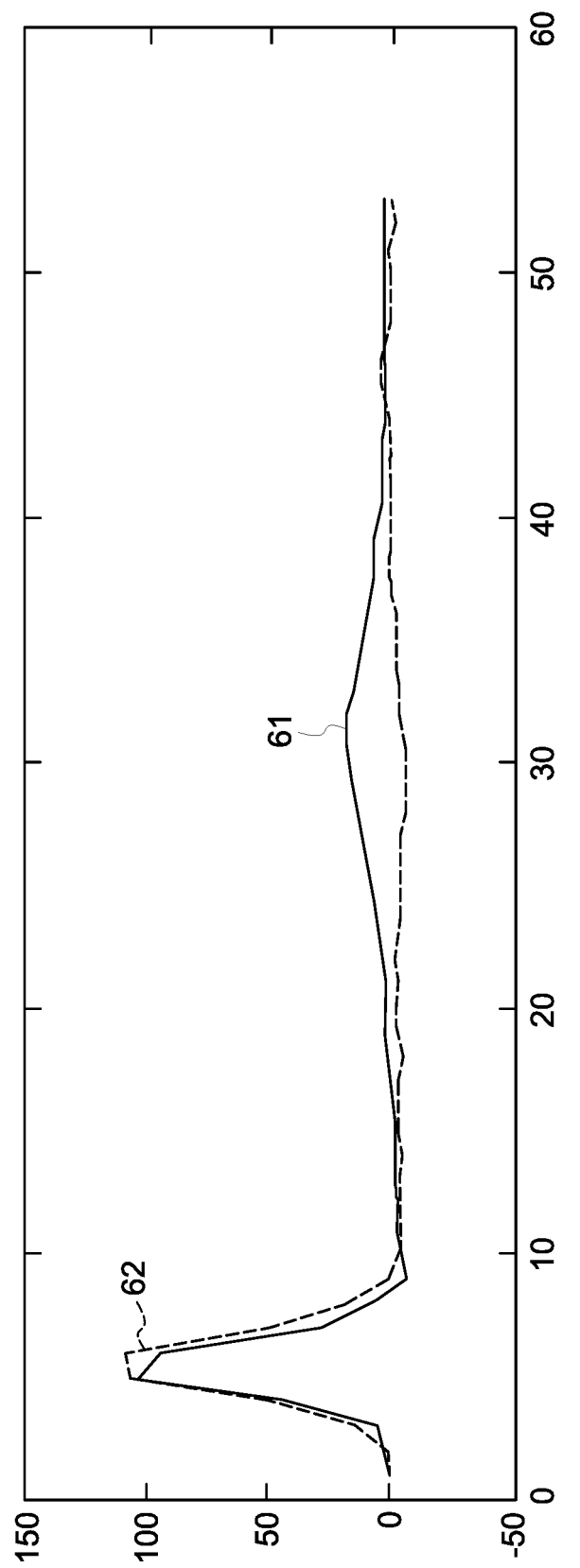
FIG. 4A is graph comparing exemplary average cardiac waveforms during sinus rhythm versus during atrial fibrillation.
Figure 4B:
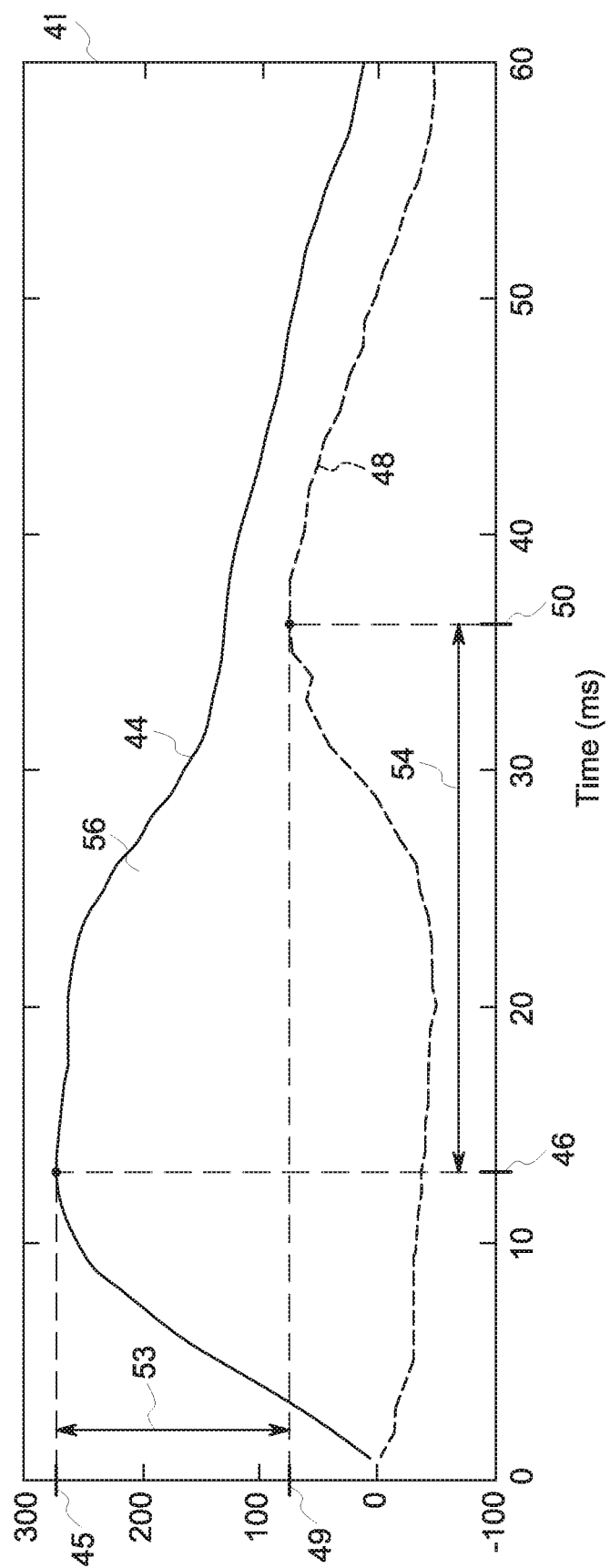
FIG. 4B is a graph comparing exemplary average pulse waveforms during normal sinus rhythm versus during AFIB.

FIGS. 4A and 4B provide comparison graphs of QRS complexes and average pulse waveforms 44, 48, respectively, during sinus rhythm and atrial fibrillation. FIG. 4A depicts an average sinus cardiac waveform 61 taken by averaging QRS complexes for cardiac cycles exhibiting normal sinus rhythm (NSR), and an average arrhythmia cardiac waveform generated based on QRS complexes for cardiac cycles where AFIB was detected. FIG. 4B is an exemplary comparison graph 41 depicting an average sinus pulse waveform 44 generated as an average time sections of pulse waveform data 34 recorded for cardiac cycles displaying NSR, and an average arrhythmia pulse waveform 48 calculated based on time sections of pulse waveform data 34 for cardiac cycles where AFIB was detected. As is evident by the comparison graph, the AFIB caused a significant change in arterial blood flow for the patient, as represented by the comparison between the average sinus pulse waveform 44 and the average arrhythmia pulse waveform 48.

In certain embodiments, the arrhythmia severity indicator 40 may comprise a comparison graph 41 along the lines of that depicted in FIG. 4B to visually display the differences between the average waveforms 44 and 48. Alternatively or additionally, the arrhythmia severity indicator 40 may include numerical values representing the differences between the waveforms. In various examples, the arrhythmia severity indicator value(s) may be based on differences in the peak amplitudes 45, 49 of the respective average waveforms 44, 48. For example, a peak amplitude difference 53 may be calculated as difference between the peak amplitude 45 of the average sinus pulse waveform 44 and the peak amplitude 49 of the average arrhythmia pulse waveform 48. Alternatively or additionally, the severity indicator value(s) may be based on a peak time difference 54 between the peak time 46 of the average sinus pulse waveform 44 and the peak time 50 of the average arrhythmia pulse waveform 48. Alternatively or additionally, the arrhythmia severity indicator value(s) may be based on the difference integral of area 56 between the average sinus pulse waveform 44 and the average arrhythmia pulse waveform 48. In still other embodiments, the arrhythmia severity indicator value(s) may be based on the duration of the average waveform 44, 48, such as the duration that the average waveform 44, 48 includes values above a predetermined amplitude.

In certain embodiments, the severity indicator value(s) may be compared to one or more corresponding severity thresholds to alert the clinician of a severe AFIB or other arrhythmia event. Alternatively or additionally, the severity indicator value(s) may be provided in conjunction with an AFIB alarm—e.g., providing an auditory or textual alert providing "AFIB with 47% decrease in pulse amplitude"—which can provide contextual information that helps caregivers properly prioritize an AFIB alarm. For example, the alarm 42 may be a visual alarm generated on the display 18 and/or an auditory alarm generated via a speaker 19 associated with the patient monitor 10. Alternatively or additionally, the alarm 42 may be generated by other patient alarming means provided in a healthcare facility, such as at a central patient monitoring station or nurse's station, or an alarm generated at a portable digital device (e.g., a pager, cell phone, tablet, etc.) for the relevant clinician.

FIG. 5 is a system diagram of an exemplary computing system 200 that includes a processing system 206, storage system 204, software 202, communication interface 208 and a user interface 210. The processing system 206 loads and executes software 202 from the storage system 204, including the arrhythmia detection module 12 and the arrhythmia analysis module 14, which are applications within the software 202. Each of the modules 12, 14 includes computer-readable instructions that, when executed by the computing system 200 (including the processing system 206), direct the processing system 206 to operate as described in herein in further detail, including to execute the steps to detect and analyze the severity of an arrhythmia.

Although the computing system 200 as depicted in FIG. 5 includes one software 202 encapsulating one arrhythmia detection module 12 and one arrhythmia analysis module 14, it should be understood that one or more software elements having one or more modules may provide the same operation. Similarly, while description as provided herein refers to a computing system 200 and a processing system 206, it is to be recognized that implementations of such systems can be performed using one or more processors, which may be communicatively connected, and such implementations are considered to be within the scope of the description.

The processing system 206 includes the processor 17, which may be a microprocessor, a general purpose central processing unit, an application-specific processor, a microcontroller, or any other type of logic-based device. The processing system 206 may also include circuitry that retrieves and executes software 202 from storage system 204. Processing system 206 can be implemented within a single processing device but can also be distributed across multiple processing devices or sub-systems that cooperate in executing program instructions.

The storage system 204, which includes the database 20, can comprise any storage media, or group of storage media, readable by processing system 206, and capable of storing software 202. The storage system 204 can include volatile and non-volatile, removable and non-removable media implemented in any method or technology for storage of information, such as computer-readable instructions, data structures, program modules, or other data. Storage system 204 can be implemented as a single storage device but may also be implemented across multiple storage devices or sub-systems. For example, the software 202 may be stored on a separate storage device than the database 20. Likewise, database 20 can be stored, distributed, and/or implemented across one or more storage media or group of storage medias. Similarly, the database 20 may encompass multiple different sub-databases at different storage locations and/or containing different information which may be stored in different formats. The database 20 is configured to store the cardiac potentials 32, arrhythmia indicators 33, pulse waveform data 34, the average pulse waveforms 44, 48 and other pulse information 36, 38, and the arrhythmia severity indicators 40. Storage system 204 can further include additional elements, such a controller capable of communicating with the processing system 206.

Examples of storage media include random access memory, read only memory, optical discs, flash memory, virtual memory, and non-virtual memory, magnetic sets, magnetic tape, magnetic disc storage or other magnetic storage devices, or any other medium which can be used to store the desired information and that may be accessed by an instruction execution system, as well as any combination or variation thereof, or any other type of storage medium. Likewise, the storage media may be housed locally with the processing system 206, or may be distributed in one or more servers, which may be at multiple locations and networked, such as in cloud computing applications and systems. In some implementations, the storage media can be a non-transitory storage media. In some implementations, at least a portion of the storage media may be transitory.

The communication interface 208 interfaces between the elements within the computing system 200 and external devices, such as to facilitate receipt of cardiac potentials from the ECG monitor 3 and/or pulse waveform data from the arterial blood flow monitor 5, UI devices such as the display 18 and speakers 19 (and/or user input devices such as a touchscreen or keyboard), and/or to facilitate communication with a central network of the healthcare facility (such as communicating the output values for storage in the patient's medical record).

Figure 6:
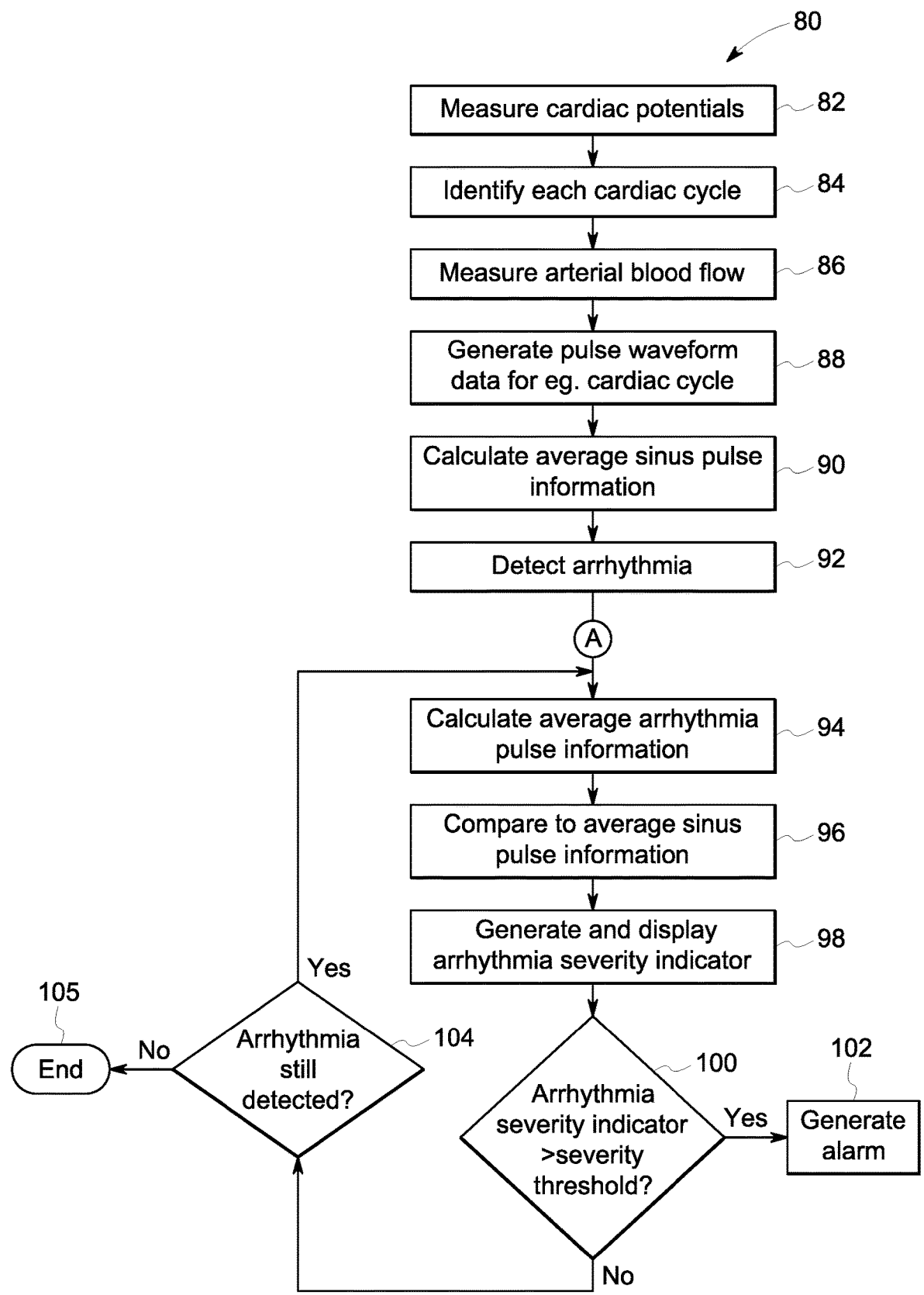
FIGS. 6 and 7 depict exemplary methods, or portions thereof, of monitoring cardiac arrhythmias of a patient.

FIG. 6 depicts one embodiment of a method 80 of monitoring cardiac arrhythmias. Cardiac potentials are measured at step 82, such as via an ECG monitor 3 and ECG electrodes 4 connected to the patient. Each cardiac cycle is identified at step 84, such as based on detection of each R peak. The arterial blood flow is measured at step 86, such as via a pulse oximetry probe 6 connected to a pulse oximeter 5 (or an invasive blood pressure probe connected to an invasive blood pressure monitor). Pulse waveform data is generated for each cardiac cycle at step 88, such as the time section of pulse waveform data timed off of the detection of the QRS complex, as described above. Average sinus pulse information is calculated at step 90, such as the average sinus pulse waveform 44, the peak amplitude 45, the peak time 46, the waveform duration, etc. In various embodiments, the average sinus pulse information may comprise any one or more of such values, which may be stored in database 20 for later comparison and use for arrhythmia analysis. Once an arrhythmia is detected at step 92, then average arrhythmia pulse information is calculated at step 94. Calculation of the average arrhythmia pulse information follows the steps and procedures for calculating the average sinus pulse information, except that the average arrhythmia pulse information is based on pulse waveform data collected after the arrhythmia was detected. Once enough pulse waveform data has been gathered to reliably determine the average arrhythmia pulse information 38, then the average arrhythmia pulse information 38 is compared to the average sinus pulse information 36 at step 96. The arrhythmia severity indicator is generated and displayed at step 98. At step 100, the arrhythmia severity indicator is compared to a severity threshold. If the severity threshold is exceeded, then an alarm is generated at step 102 to advise a clinician of the severe arrhythmia. If not, then the analysis continues as new arrhythmic pulse information is detected until the arrhythmia is no longer detected at step 104. At that point, the arrhythmia analysis is ended at step 105.

Figure 7:
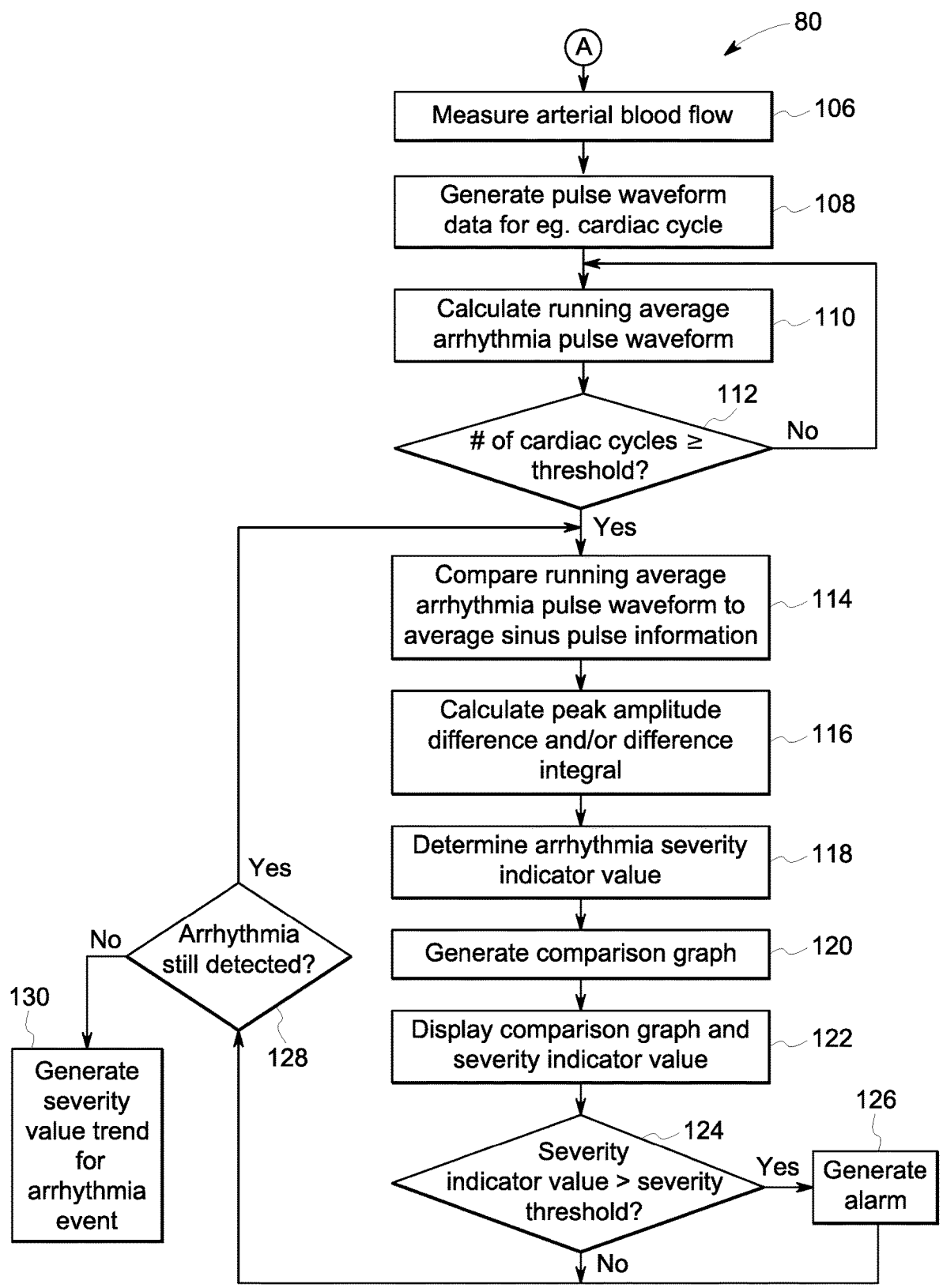

FIG. 7 depicts another embodiment of method steps executed once an arrhythmia is detected, such as following steps 82-92 represented at FIG. 6. Following the arrhythmia detection, the arterial blood flow is measured at step 106 and the pulse waveform data is generated for each cardiac cycle at step 108. A running average arrhythmia pulse waveform is calculated at step 110 based on the time section of pulse waveform data for each cardiac cycle. Thus, as new pulse waveform data comes in, the relevant time section for the new cardiac cycle is isolated and added to the running average arrhythmia pulse waveform 48. In certain embodiments, the running average arrhythmia pulse waveform may be calculated based on a predetermined number of time sections of pulse waveform data. Thereby, the running average arrhythmia pulse waveform 48 may be more responsive to changes in the pulse waveform. Other average arrhythmia pulse information may also be calculated, as described above, and all In certain embodiments, the number of time sections incorporated in the running average may be average arrhythmia pulse information may be stored in database 20. In certain embodiments, the number of time sections incorporated in the running average may be average arrhythmia pulse information an adjustable value, such as adjustable by a clinician attending to the patient, to make the average arrhythmia pulse waveform more or less responsive to changes in the pulse waveform data during the course of the arrhythmia event.

Once a threshold number of cardiac cycles is reached at step 112, then the average arrhythmia pulse waveform 48 is compared at step 114 with the previously-determined average sinus pulse waveform 44. In various embodiments, the threshold number of cardiac cycles may be any number of two or more cardiac cycles, which may be a calibrated or adjustable value determined by a clinician based on the monitoring application, the patient condition, etc. In other embodiments, the threshold number of cardiac cycles may be the same number for the number time sections incorporated in the running average at step 110.

The comparison between the running average arrhythmia pulse waveform 48 and the average sinus pulse waveform 44 may include a determination of the peak amplitude difference 53 and/or the difference integral of the area 56 between the average waveforms 44, 48. The arrhythmia severity indicator value is determined at step 118, such as based on the amplitude difference 53 and/or the difference integral of area 56. For example, the arrhythmia severity indicator value may be a value on a scale used to indicate severity, such as a numerical scale or color scale configured to and capable of quickly and easily communicating severity to an attending clinician. The arrhythmia severity indicator may be stored in database 20 and may become part of the patient medical record. A comparison graph is generated at step 120, and the comparison graph and severity indicator value are displayed at step 122, such as on the display 18 associated with patient monitor 10. If the severity indicator value exceeds the severity threshold at step 124, then an alarm is generated at step 126. The arrhythmia severity assessment continues until the arrhythmia is no longer detected at step

128. In the depicted embodiment, a severity value trend is generated at step 130 depicting the severity values calculated for the period for which the arrhythmia was detected. Such a trend is especially applicable where the average arrhythmia information is calculated as a running average of a predetermined number of cardia cycles or is calculated periodically through the arrhythmia event, such as based on predetermined time increments of pulse waveform data.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

I claim:

1. A patient monitoring system for monitoring cardiac arrhythmias, the system comprising:
    an ECG monitor configured to measure cardiac potentials during cardiac cycles;
    an arterial blood flow monitor configured to measure arterial blood flow for the cardiac cycles and generate pulse waveform data;
    an arrhythmia detection module configured to:
       detect a presence of an arrhythmia based on the cardiac potentials;
       generate an arrhythmia indicator upon detecting the presence of the arrhythmia;
    an arrhythmia analysis module configured to:
       calculate average sinus pulse information based on pulse waveform data for two or more cardiac cycles occurring when no arrhythmia is detected;
       receive an arrhythmia indicator generated by the arrhythmia detection module;
       calculate average arrhythmia pulse information based on pulse waveform data for two or more cardiac cycles occurring after the arrhythmia indicator;
       compare the average sinus pulse information and the average arrhythmia pulse information; and
       generate an arrhythmia severity indicator based on the comparison.

2. The system of claim 1, wherein the arterial blood flow monitor is one of a plethysmograph or an invasive blood pressure monitor.

3. The system of claim 1, wherein the average sinus pulse information is calculated based on predetermined time sections pulse waveform data during each of the two or more cardiac cycles occurring when no arrhythmia is detected.

4. The system of claim 3, wherein the average arrhythmia pulse information is calculated based on the predetermined time sections of pulse waveform data during each of the two or more cardiac cycles occurring after the arrhythmia indicator.

5. The system of claim 3, wherein the average sinus pulse information includes an average sinus pulse waveform and the average arrhythmia pulse information includes an average arrhythmia pulse waveform.

6. The system of claim 5, wherein the arrhythmia severity indicator includes a comparison graph depicting the average sinus pulse waveform and the average arrhythmia pulse waveform on a shared time axis.

7. The system of claim 5, wherein the comparison of the average sinus pulse waveform and the average arrhythmia pulse waveform includes determination of at least one of a peak amplitude difference between the average sinus pulse waveform and the average arrhythmia pulse waveform or a difference integral between the average sinus pulse waveform and the average arrhythmia pulse waveform.

8. The system of claim 7, wherein the arrhythmia severity indicator includes a value determined based on at least one of the peak amplitude difference or the difference integral.

9. The system of claim 8, wherein the arrhythmia analysis module is further configured to compare the arrhythmia severity indicator value to a severity threshold, and generate an alarm if the arrhythmia severity indicator value exceeds the severity threshold.

10. The system of claim 1, wherein the comparison includes calculation of at least one of a peak amplitude difference or a peak time difference based on the average sinus pulse information and the average arrhythmia pulse information, and the arrhythmia severity indicator is a value determined based on the peak amplitude difference and/or the peak time difference.

11. A method of monitoring cardiac arrhythmias, the method comprising:
    measuring cardiac potentials with an ECG monitor during cardiac cycles;
    measuring arterial blood flow for the cardiac cycles with an arterial blood flow monitor and generating pulse waveform data;
    calculating average sinus pulse information based on pulse waveform data for two or more cardiac cycles for which no arrhythmia is detected;
    detecting a presence of an arrhythmia based on the cardiac potentials;
    calculating average arrhythmia pulse information based on pulse waveform data for two or more cardiac cycles after detecting the arrhythmia;
    comparing the average sinus pulse information and the average arrhythmia pulse information; and
    generating an arrhythmia severity indicator based on the comparison.

12. The method of claim 11, wherein the arterial blood flow monitor is one of a plethysmograph or an invasive blood pressure monitor.

13. The method of claim 11, wherein calculating the average sinus pulse information includes averaging time sections of pulse waveform data during each of the two or more cardiac cycles occurring when no arrhythmia is detected.

14. The method of claim 13, wherein calculating the average arrhythmia pulse includes averaging the time sections of pulse waveform data during each of the two or more cardiac cycles occurring after detecting the arrhythmia.

15. The method of claim 13, wherein the average sinus pulse information includes an average sinus pulse waveform and the average arrhythmia pulse information includes an average arrhythmia pulse waveform.

16. The method of claim 15, wherein generating the arrhythmia severity indicator includes generating a comparison graph depicting the average sinus pulse waveform and the average arrhythmia pulse waveform with respect to a single time axis.

17. The method of claim 15, wherein comparing the average sinus pulse waveform and the average arrhythmia pulse waveform includes calculating at least one of a peak amplitude difference between the average sinus pulse waveform and the average arrhythmia pulse waveform or a difference integral between the average sinus pulse waveform and the average arrhythmia pulse waveform.

18. The method of claim 17, wherein the arrhythmia severity indicator is a value determined based on at least one of the peak amplitude difference or the difference integral.

19. The method of claim 18, further comprising comparing the arrhythmia severity indicator value to a severity threshold, and generating an alarm if the arrhythmia severity indicator value exceeds the severity threshold.

20. The method of claim 11, wherein the comparing step includes calculating a peak amplitude difference based on the average sinus pulse information and the average arrhythmia pulse information, and the arrhythmia severity indicator is a value determined based on the peak amplitude difference.

* * * * *